(12) United States Patent (10) Patent No.: US 7,828,758 B2
Clements et al. (45) Date of Patent: Nov. 9, 2010

(54) ANKLE SUPPORT WITH CALCANEOUS CONTROL STRAP

(75) Inventors: Karen M. Clements, Knoxville, TN (US); Autry O. V. DeBusk, Knoxville, TN (US); Michael D. Modglin, Braselton, GA (US); John H. Krusenklaus, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 230 days.

(21) Appl. No.: 12/055,487

(22) Filed: Mar. 26, 2008

(65) Prior Publication Data

US 2009/0247920 A1 Oct. 1, 2009

(51) Int. Cl.
  *A61F 5/00* (2006.01)
(52) U.S. Cl. .......................... 602/23; 602/27
(58) Field of Classification Search ............ 602/16–28, 602/60–62; 128/882
  See application file for complete search history.

(56) References Cited

U.S. PATENT DOCUMENTS

| 1,465,970 | A |   | 8/1923 | Cleveland et al. |
| 3,699,959 | A |   | 10/1972 | Garrahan et al. |
| 4,392,487 | A |   | 7/1983 | Selner et al. |
| 4,844,094 | A |   | 7/1989 | Grim |
| 4,869,267 | A |   | 9/1989 | Grim et al. |
| 4,948,092 | A |   | 8/1990 | Kasper et al. |
| 4,964,402 | A |   | 10/1990 | Grim et al. |
| 5,026,339 | A |   | 6/1991 | Kasper |
| 5,027,801 | A |   | 7/1991 | Grim |
| 5,067,486 | A | * | 11/1991 | Hely ........................... 602/27 |
| 5,088,478 | A |   | 2/1992 | Grim |
| 5,209,722 | A | * | 5/1993 | Miklaus et al. ............... 602/27 |
| 5,348,530 | A |   | 9/1994 | Grim et al. |
| 5,445,602 | A |   | 8/1995 | Grim et al. |
| 5,620,413 | A |   | 4/1997 | Olson |
| 5,716,335 | A |   | 2/1998 | Iglesias et al. |
| 5,795,316 | A |   | 8/1998 | Gaylord |
| 5,951,504 | A |   | 9/1999 | Iglesias et al. |
| 6,053,884 | A |   | 4/2000 | Peters |
| 6,454,733 | B1 |   | 9/2002 | Krusenklaus |
| 6,460,275 | B1 |   | 10/2002 | Bennett et al. |
| 6,524,266 | B1 |   | 2/2003 | Peters |
| 6,602,215 | B1 | * | 8/2003 | Richie, Jr. ..................... 602/27 |
| 6,749,578 | B2 |   | 6/2004 | Peters |
| 6,858,017 | B2 |   | 2/2005 | Peters |
| D552,744 | S | * | 10/2007 | Verkade et al. ............ D24/192 |

\* cited by examiner

*Primary Examiner*—Michael A. Brown
(74) *Attorney, Agent, or Firm*—Luedeka, Neely & Graham, PC

(57) ABSTRACT

A foot support having straps which receive the calcaneous and wrap around the midfoot in a tensioned state for stabilizing the rearfoot and the midfoot to avoid excessive inversion and eversion of the foot.

7 Claims, 8 Drawing Sheets

US 7,828,758 B2

ANKLE SUPPORT WITH CALCANEOUS CONTROL STRAP

FIELD

This disclosure relates to the field of ankle supports. More particularly, this disclosure relates to an ankle support wearable alone or inside a shoe which does not limit a normal gait and stabilizes an ankle or rear portion of the foot and a midfoot portion of the foot against undesired inversion and eversion.

BACKGROUND

Ankle sprains typically result from an incidence of either excessive inversion or excessive eversion. Inversion, which is the more common injury cause, is characterized as internal rotation of the ankle joint. Eversion is characterized as external rotation of the ankle joint. Movement of the midfoot is also associated with inversion and eversion.

For example, in the typical ankle injury, an off-centered force, such as landing from a jump with the foot turned or experiencing a strong side-directed impact on the lower leg with the foot planted, causes the foot to invert or evert relative to the lower leg. As with other body joints, the ankle joint is held together, supported and cushioned by a number of non-bony or soft tissues, such as muscles, ligaments, tendons, and cartilage. When the off-centered force results in inversion or eversion of the foot relative to the lower leg in excess of the natural limits of the soft tissue structures, soft tissue damage of varying degrees of severity occurs. Such injuries can include stretching or tearing of those soft tissues and, if severe enough, damage or fracture to the bones which make up the ankle joint, lower leg and foot.

Ankle supports are often worn as treatment for an ankle sprain or to prevent an ankle sprain. Desirably, an ankle support is lightweight, compact so as to be able to be worn inside a shoe, supports the ankle and foot to limit inversion and eversion, but does not otherwise limit the flexion motions associated with the toe-up and toe-down motions of a normal gait. Prior devices have disadvantages in regards to one or more of these considerations and improvement is desired.

SUMMARY

The above and other needs are met by a foot support for controlling motion of a foot of a user.

In a preferred embodiment, the support includes a receiver configured for receiving a calcaneous bone of the foot and a pair of straps extending from the receiver and positionable to extend in opposite directions underneath a midfoot portion of the foot and to extend in opposite directions over an upper portion of the midfoot portion of the foot. The straps are tensionable and securable in the tensioned state to limit undesired movement of the foot.

In another preferred embodiment, the support is provided as an ankle support that includes a body portion configured to be positioned on a lower leg of the user adjacent the ankle joint; a foot plate hingedly coupled to the body portion and configured for supporting the foot of the user; and a calcaneous control strap system for limiting movement of a subtalar joint of the foot relative to the lower leg portion.

The calcaneous control strap system includes a receiver located adjacent the body portion and the foot plate and configured for receiving a calcaneous bone of the subtalar joint and a pair of straps extending from the receiver. The straps are positionable to extend in opposite directions underneath a portion of the foot when the foot is supported by the foot plate and to extend in opposite directions over an upper portion of the mid foot, the straps being tensionable and securable in the tensioned state to limit tilting of a talus portion of the subtalar joint relative to the lower leg of the user and effectively limit undesired movement of the subtalar joint.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

The disclosure relates to an ankle support 10 that is lightweight, compact so as to be wearable inside a shoe if desired, does not limit a normal gait, and stabilizes an ankle against inversion and eversion. The support 10 is useful for both avoiding ankle sprain, and for stabilizing a previously injured ankle.

Figure 1A:
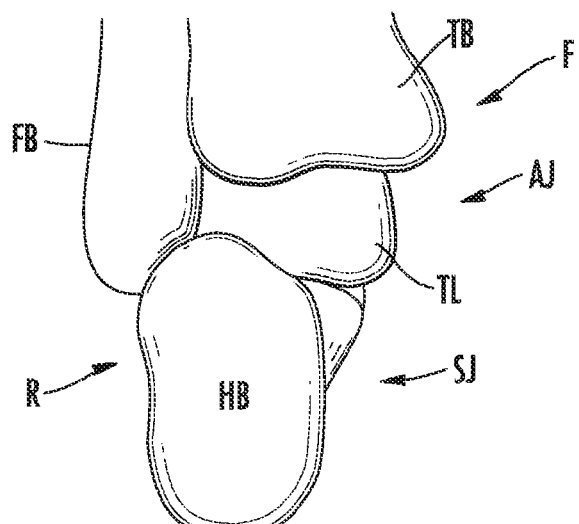
FIGS. 1A-1C are posterior views of the ankle joint and subtalar joint in conditions of neutral, inversion, and eversion.

With reference to FIG. 1A, the support 10 is configured for application to a foot to stabilize a rearfoot portion R of a foot F, particularly to an ankle including a talocrural joint commonly called an ankle joint AJ composed of three bones: tibia TB which forms the inside or medial portion of the ankle, fibula FB which forms the lateral or outside portion of the ankle, and talus TL underneath. The ankle joint AJ provides up and down motion of the foot (dorsiflexion and plantarflexion). Below the lower leg is a second part of the ankle joint, known as the talocalcaneal joint or the subtalar joint (SJ) which includes the talus TL on top and calcaneus or heel bone HB on the bottom. The subtalar joint SJ allows side to side motion of the foot, i.e, inversion and eversion of the rearfoot portion R, but plays no role in dorsiflexion or plantarflexion of the foot.

Figure 1B:
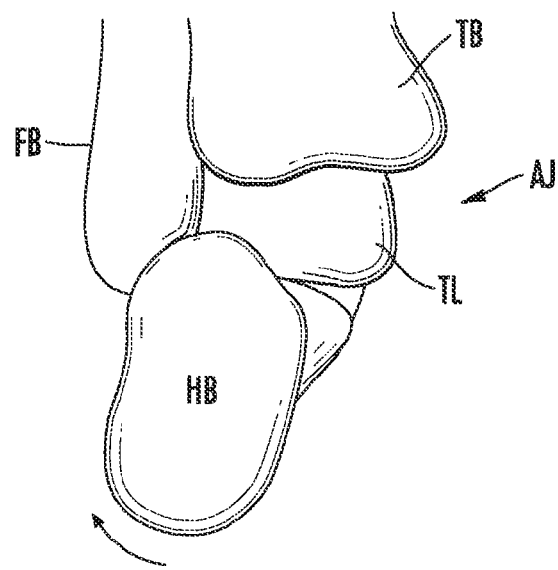
Figure 1C:
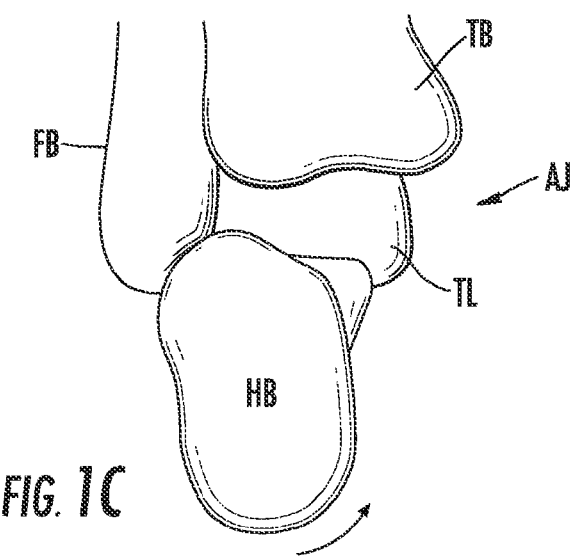

The support 10 is configured to not substantially limit the up/down motion of the ankle joint AJ, but to substantially stabilize the subtalar joint SJ against side to side motion, and hence inversion and eversion of the foot. In this regard, FIG. 1A shows the subtalar joint SJ in a neutral condition, FIG. 1B shows the subtalar joint SJ in a condition of excessive inversion, and FIG. 1C shows the subtalar joint SJ in a condition of excessive eversion, with the arrows showing the direction of movement of the calcaneous HB. The support 10, when properly installed, restricts motion of the heel bone HB to prevent injurious movement of the ankle joint AJ.

Figure 2:
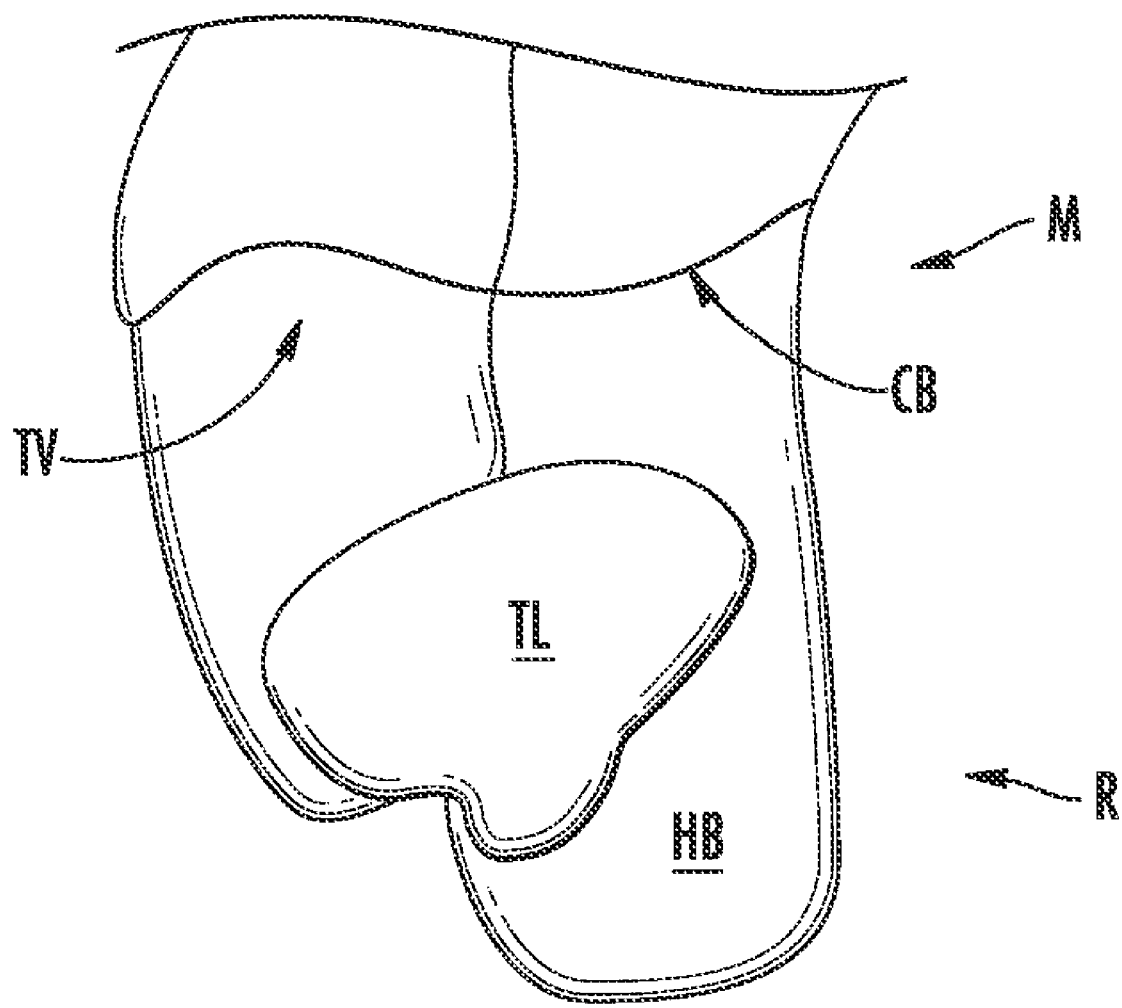
FIG. 2 is a top view of rearfoot and midfoot portions of a foot.
Figure 3:
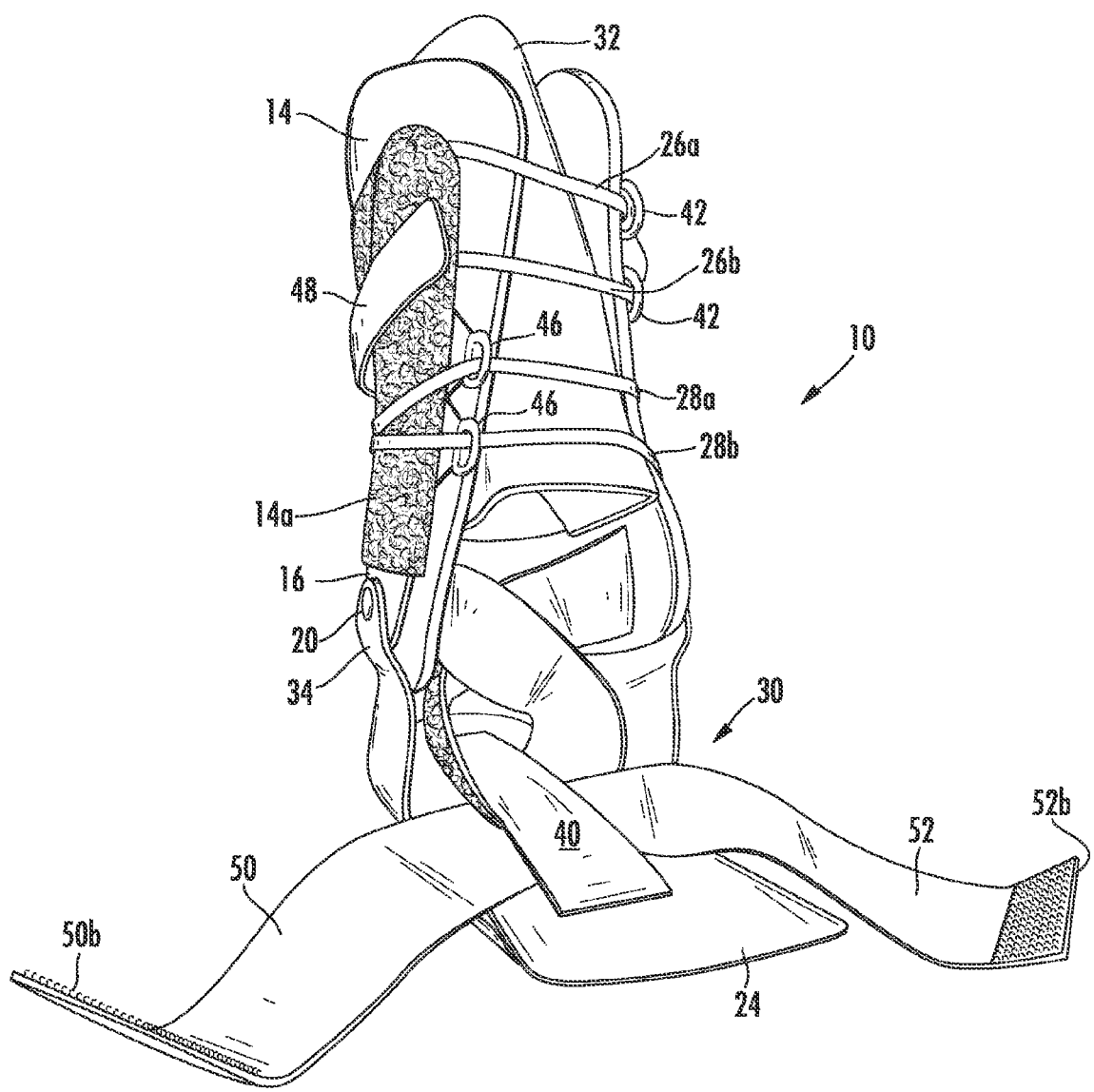
FIG. 3 is a perspective view of a foot support according to a preferred embodiment of the disclosure.

With reference to FIG. 2, it has also been observed that the support 10 is also useful to limit undesired movement of a midfoot portion M of the foot F. The midfoot M is composed of a talonavicular joint TV and a calcaneobuboid joint CB of the foot F. These joints permit toe-in and toe-out movement of foot F. These joints and their movements are associated with foot inversion and eversion and it has been observed that use of the support 10 is also useful to stabilize these joints against undesired excessive movements associated with inversion and eversion of the foot.

In this regard, "injurious movement" will be understood to movements which result in excessive inversion or excessive eversion or other excessive movement or motion of the subtalar joint SJ and/or the midfoot M which exceeds the range of movement or motion that can be experience and not be injured.

It has been observed that avoiding the excessive inversion or eversion of the foot relative to the lower leg is desirable to prevent injury to the soft tissue structures of the ankle joint. Also, once the ankle joint has been injured, it is preferable to approximate the joint and healing structures and soft tissues into a normal bio-mechanical configuration, so that the joint can heal properly. Bio-mechanically, excess inversion or eversion requires movement, especially rotational movement, of the subtalar joint about a horizontal axis aligned with the foot.

In reference to the alignment of the bony components of the ankle joint in FIG. 1A, which represents a neutral orientation, it can be readily seen that when the calcaneous HB, talus TL, tibia TB and fibula FB are in approximate vertical alignment, the talus TL is effectively sandwiched in between the lower leg bones (tibia TB/fibula FB) and the calcaneous HB. This alignment bio-mechanically stabilizes the ankle joint AJ to prevent excessive tilting of the talus TL relative to the tibia TB and the fibula FB, thus effectively limiting undesired movement of the subtalar joint SJ. The talus TL is not in this sandwiched or bio-mechanically stabilized orientation and thus is able to move to the inverted and everted orientations represented in FIGS. 1B and 1C.

Accordingly, for excessive inversion or eversion to occur, the calcaneous HB must be out of the described bio-mechanical alignment with the talus TL and the lower leg bones (tibia TB and fibula FB) before movement of the subtalar joint SJ can occur. Thus, it has been observed that maintaining the desired positioning of the calcaneous HB can provide an inherent bio-mechanical structural mechanism for the avoiding undesired inversion or eversion of the foot relative to the lower leg in the prevention or treatment of ankle injuries. This is effectively accomplished by the support 10 which advantageously integrates a calcaneous control strap system to maintain the subtalar joint SJ in alignment with the talus TL and thereby provide improved bio-mechanical control of the ankle joint to prevent undesired or excessive inversion or eversion.

With reference to FIGS. 3-8, the support 10 includes an upper boot assembly 12 having a generally U-shaped flexible body 14, a pair of rigid uprights 16 and 18, a pair of hinges 20, a rigid foot plate 22, a foot liner 24, a pair of laces 26 and 28, and a calcaneous control strap system 30.

The flexible body 14 is configured to substantially surround the lower leg of the user and conform thereto when the laces 26 and 28 are tensioned. The body 14 also provides an anchoring point for securing the calcaneous control strap system 30 in a tensioned state. The flexible body 14 may be made of a padded nylon material and includes a pair of sleeves 14a and 14b on opposite sides thereof which are configured for securably receiving the uprights 16 and 18 and maintaining the uprights 16 and 18 on opposite sides of the leg of the user. The exterior surfaces of the sleeves 14a and 14b are made of a loop material (or a hook material) for releasably engaging a hook material (or a loop material) associated with the laces 26 and 28 or the strap system 30. A tongue 32 made of a soft flexible material may be provided to span the gap at the front of the body 14 in the manner of the tongue of a boot for comfort when the laces 26 and 28 are tensioned. In this regard, the interior of the flexible body 14 preferably includes a soft surface that acts in the manner of a loop material to releasably engage a hook material. Accordingly, the tongue 32 may include loop material to facilitate removably engaging the tongue 32 with the body 14.

The uprights 16 and 18 are each made of a lightweight and substantially rigid material, such as aluminum or plastic having sufficient rigidity so as to substantially avoid bending during use. Preferred materials include glass-filled nylon polypropylene. The uprights 16 and 18 are configured to for within the sleeves 14a and 14b to lie on opposite sides of the leg of the user, and extend up the sides of the shin or lower leg from a location adjacent the lowermost portions of the tibia TB and the fibula FB. For the purpose of example, the uprights 16 and 18 have a length of about 6 inches and a width of about 1¾ inch.

The hinges 20 hingedly connect the lower ends of uprights 16 and 18 to the rigid foot plate 22, with the hinge axis permitting the lower ends of the uprights 16 and 18 to pivot so as to not limit the up/down motion of the ankle joint AJ. The hinges 20 do not permit side to side motion of the lower ends of the uprights, such that the rigidity of the uprights 16 and 18 and the rigidity of the foot plate 22 limit side to side motion of the assembled uprights 16 and 18 and the foot plate 22. The hinges 22 may be provided as by pins through cooperating apertures or the like.

The rigid foot plate 22 is preferably of one-piece construction and made of a thin, lightweight and substantially rigid material, such as aluminum or plastic having sufficient rigidity so as to substantially avoid bending during use. The plate 22 preferably has a substantially uniform thickness of about 4.5 mm or less, so as to be sufficiently thin to avoid with interference with fit when installing within a shoe. The foot plate 22 is generally rectangular, having a rounded heel end and an opposite square end, with the length selected so that when the heel end underlies the heel of the user the square end is located slightly behind the small toe of the user so as to not interfere with the flex of the toes during walking. The width of the foot plate 22 is selected to be just slightly greater than the width of the foot of the user.

A pair of extensions 34 and 36 extend upwardly from opposite sides of the foot plate 22 at a location slightly forward of the heel end so as to generally align with the tibia TB and the fibula FB when installed on a user. The extensions 34 and 36 have a height selected so that the upper ends of the extensions 34 and 36 are adjacent opposite sides of the ankle joint AJ when installed. When the hinges 20 are installed on the extensions 34 and 36, the hinge axis of the uprights 16 and 18 are adjacent to the axis of the ankle joint AJ to permit the lower ends of the uprights 16 and 18 to pivot so as to not limit the up/down motion of the ankle joint AJ.

The foot liner 24 is configured to overlie the foot plate 22 and is made of a thin, flexible material to pad and wick moisture from the foot. The foot liner 24 is releasably secured to the plate 22 as by mating pieces of hook and loop material 38. The heel end of the liner 24 is preferably cup-shaped to seat the heel of the foot. An anchor sleeve 40 is located on the upper surface of the foot liner 24 so as to substantially underlie the arch of the foot of the user during use. The anchor sleeve 40 is provided, for example, by a strip of fabric material longitudinally aligned with the length of the liner 24, with the ends thereof secured to the liner 24, as by stitches, and the remainder unsecured so as to provide a through passage 40a.

As described in more detail below, straps associated with the strap system 30 are passed through the passage 40a of the anchor sleeve 40 so as to anchor them in location relative to the length of the foot, but permit them to be tensioned around the foot.

The lace 26 preferably includes a pair of laces 26a and 26b which extend through guides 42. The terminal ends of the laces 26a and 26b are affixed, as by threads, to the body 14, and the distal ends attach to a common member 44 provided as by a strip of hook (or loop) material which releasably engages the loop (or hook) material of the sleeve 14a. The lace 28 is similarly configured and includes laces 28a and 28b which extend through guides 46 and a common member 48 which releasably engages the loop (or hook) material of the sleeve 14b.

The calcaneous control strap system 30 is configured to be installed on the foot of the user to effectively stabilize and limit movement of the subtalar joint SJ, while not interfering with up/down motion of the ankle joint AJ. In a preferred embodiment, the strap system 30 is provided by a pair of straps 50 and 52 having anchored ends 50a and 52a, respectively, and opposite free ends 50b and 52b. The straps 50 and 52 are made of a flexible and slightly elastic material so as to conform to the portions of the foot around which it is placed. A suitable material or the straps 50 and 52 is an elastic hook and loop strap material available under the designation VEL-STRETCH from Velcro Industries B.V.

Figure 5:
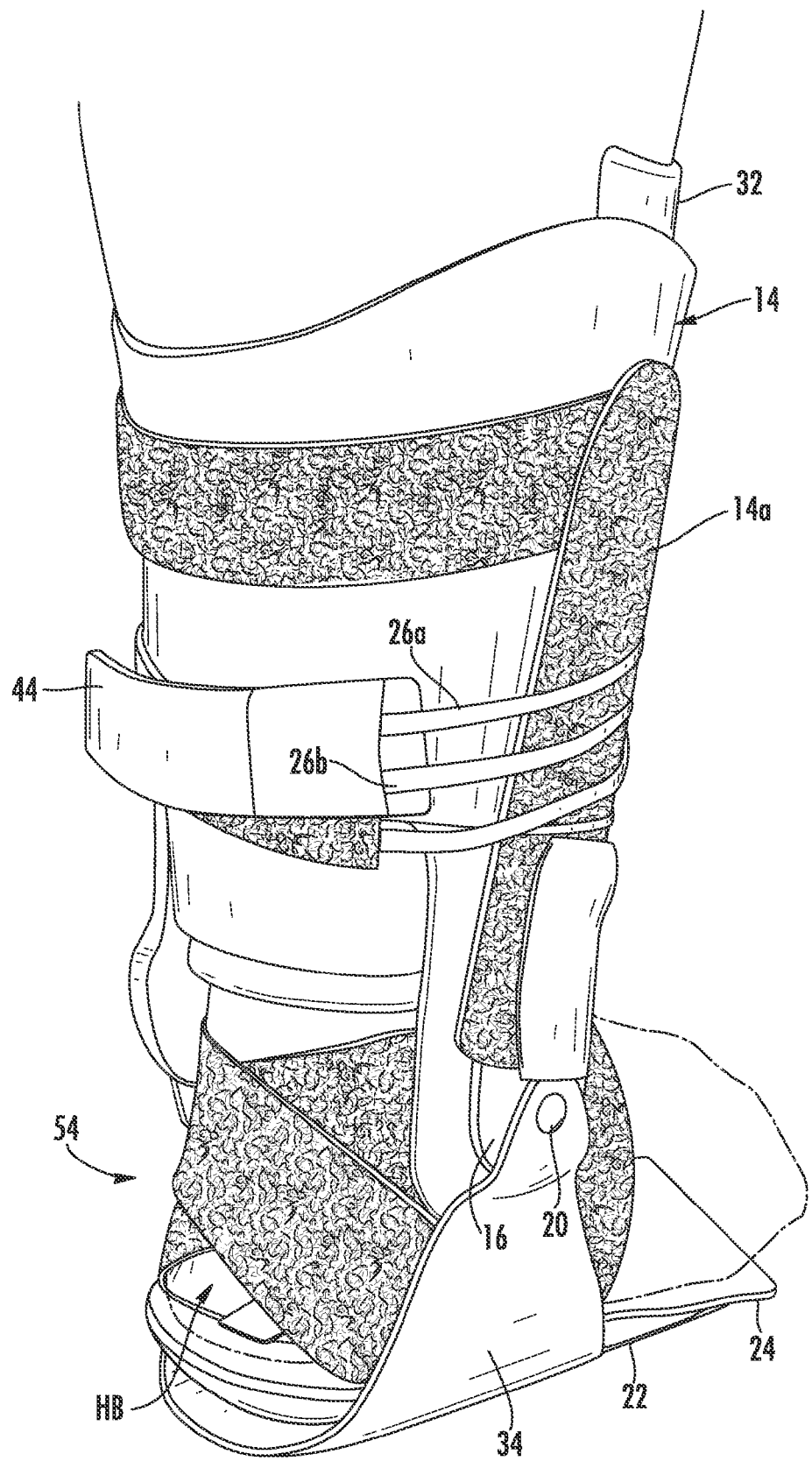
FIG. 5 is a rear view of the support of FIG. 4.

The anchored ends 50a and 52a are secured on opposite sides of the interior of the body 14, as by stitches or the like, so as to be located on opposite sides of the ankle joint AJ. The straps 50 and 52 are overlapped at a location near the anchored ends 50a and 52a so as to provide a calcaneous receiver 54 that can be positioned around the back of the calcaneous HB and fittingly receive the calcaneous HB (FIG. 5). Stitches or the like are preferably provided at the location of the receiver 54 to secure the straps 50 and 52 together at this location. The free ends 50b and 52b are threaded from opposite sides through the passage 40a of the anchor sleeve 40 and are thus positioned to be wrapped around the talonavicular joint of the foot of the user. The free ends 50b and 52b include hook (or loop) material so as to be releasably engageable to the loop (or hook) material of the sleeves 14a and 14b.

Figure 4:
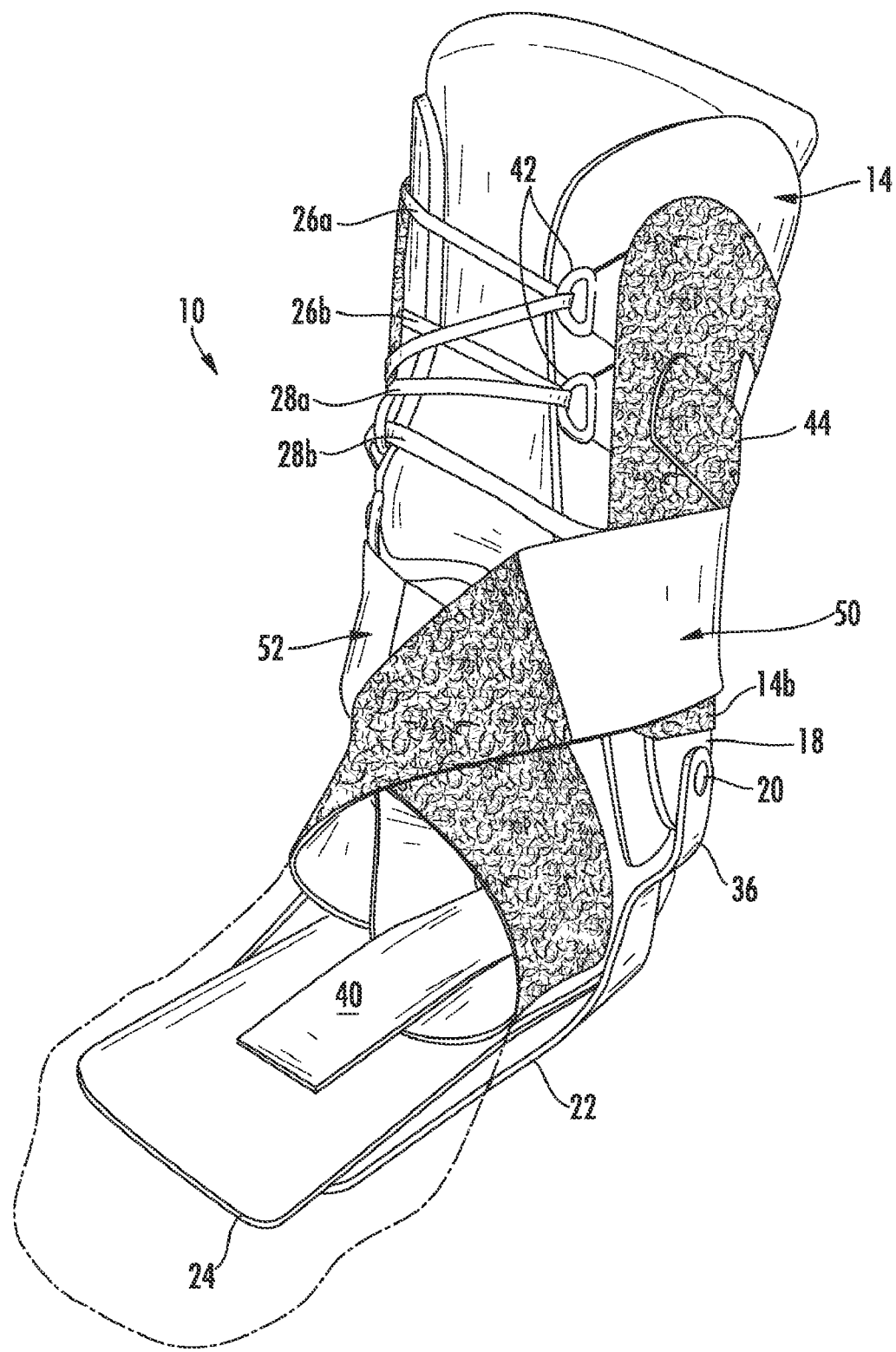
FIG. 4 is a perspective view showing the support of FIG. 3 installed on a foot of a user.
Figure 6:
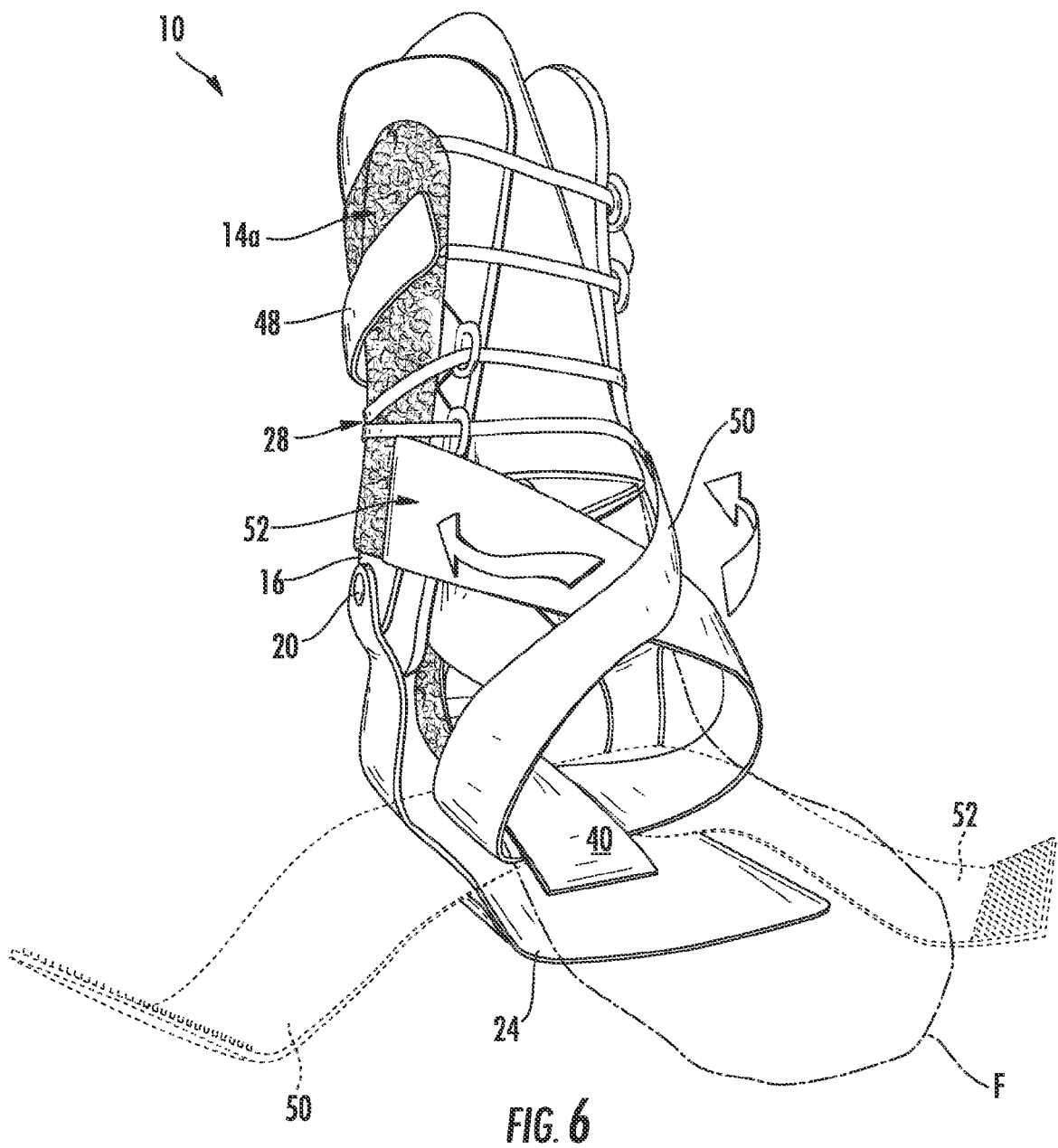
FIG. 6 shows tensioning of a calcaneous strap of the support of FIG. 4.
Figure 7:
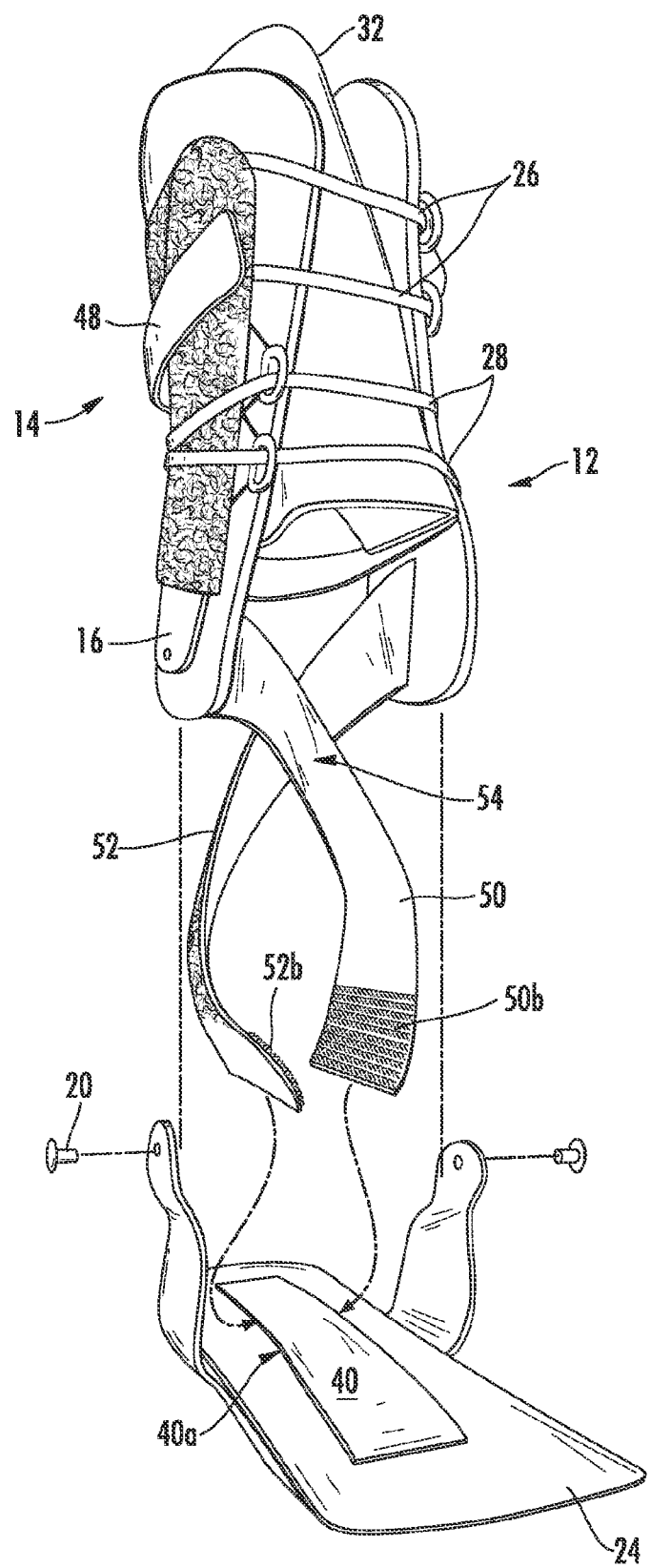
FIG. 7 is a partial exploded view of the support of FIG. 3.
Figure 8:
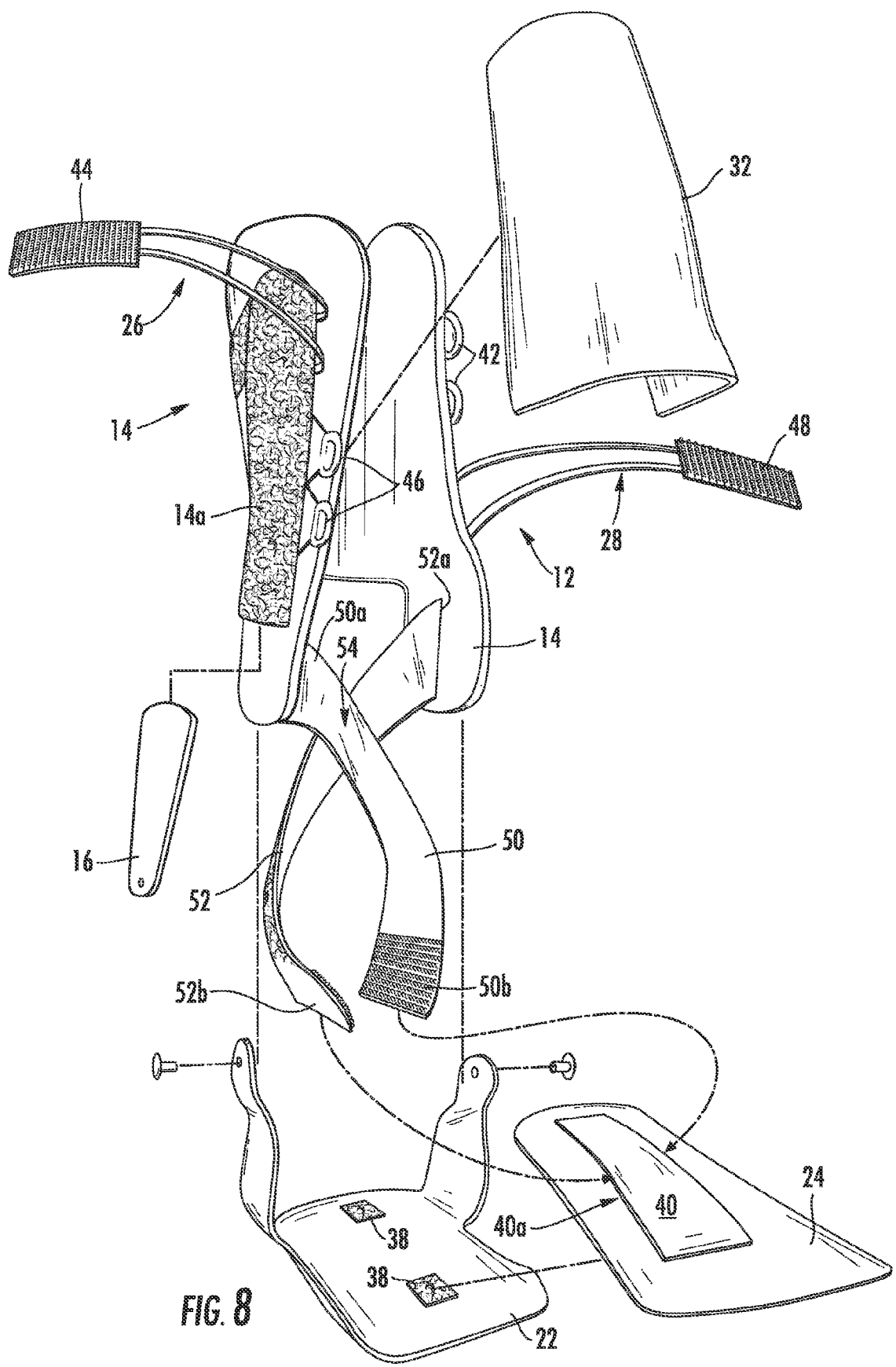
FIG. 8 is an exploded view of the support of FIG. 3.

With particular reference to FIG. 6, the support 10 is installed on the foot F (shown in phantom) by placing the foot F though the body 14 so that the foot F rests on the foot liner 24 with the receiver 54 adjacent the calcaneous HB, the straps 50 and 52 extending through the passage 40a underneath the talonavicular joint of the foot F, and the body 14 surrounding the lower leg of the user with the uprights 16 and 18 on opposite sides of the leg. The laces 26 and 28 may then be tensioned and secured to the sleeves 14a and 14b. Next, the free ends 50b and 52b are grasped and extended in opposite directions in an overlapping orientation over the top of the foot F (FIGS. 4 and 6). Additionally, the heel/foot position can be controlled to selectively invert or evert the foot before applying the straps 50 and 52.

When the desired tension is achieved in the straps 50 and 52, the ends 50b and 52b are secured to the sleeves 14b and 14a by the mating hook and loop interfaces. In this regard, it is preferred that the tension of the straps 50 and 52 be sufficient to maintain the neutral orientation orientation of the ankle joint of FIG. 1A, wherein the calcaneous HB, talus TL, tibia TB and fibula FB are in approximate vertical alignment, such that the talus TL is effectively sandwiched in between the tibia TB, the fibula FB, and the calcaneous HB. As described previously, in this condition the talus TL is limited from tilting relative to the tibia TB and the fibula FB, thus effectively limiting undesired movement of the subtalar joint SJ. It has been observed that the support 10, when properly installed, is useful to stabilize the subtalar joint without limiting the normal gait of the user.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. An ankle support for controlling motion a subtalar joint portion an ankle joint of a user, the support comprising:
   a body portion configured to be positioned on a lower leg of the user adjacent the ankle joint:
   a foot plate hingedly coupled to the body portion and configured for supporting the foot of the user; and
   a calcaneous control strap system for limiting movement of the subtalar joint relative to the lower leg portion, the calcaneous control strap system, comprising a receiver located adjacent the body portion and the foot plate and configured for receiving a calcaneous bone of the subtalar joint and a pair of straps extending from the receiver and positionable to extend in opposite directions underneath a portion of the foot when the foot is supported by the foot plate and to extend in opposite directions over an upper portion of the foot, the straps being tensionable and securable in the tensioned state to limit tilting of a talus portion of the subtalar joint relative to the lower leg of the user and effectively limit undesired movement of the subtalar joint.

2. The support of claim 1, wherein the body portion further includes a pair of rigid uprights located to lie on opposite sides of the lower leg of the user.

3. The support of claim 1, wherein the support further includes a foot liner releasably secured to the foot plate, with the foot liner including an anchor sleeve providing a passage for passage of the straps underneath the foot of the user.

4. The support of claim 1, wherein the receiver is provided by overlapping portions of the straps, with the straps each having an end adjacent the receiver that is connected to the body portion.

5. The support of claim 1, further comprising a lace for tensioning the body portion about the lower leg of the user.

6. The support of claim 5, wherein the lace comprises a plurality of laces each having an end affixed to the body portion and an opposite end comprising a common member attached to each of the laces and releasably engagable with the body portion.

7. The support of claim 1, wherein when the pair of straps extend from the receiver they are positionable to extend in opposite directions underneath a midfoot portion of the foot and limit movement of the midfoot portion of the foot when tensioned.

* * * * *